Figure 1:
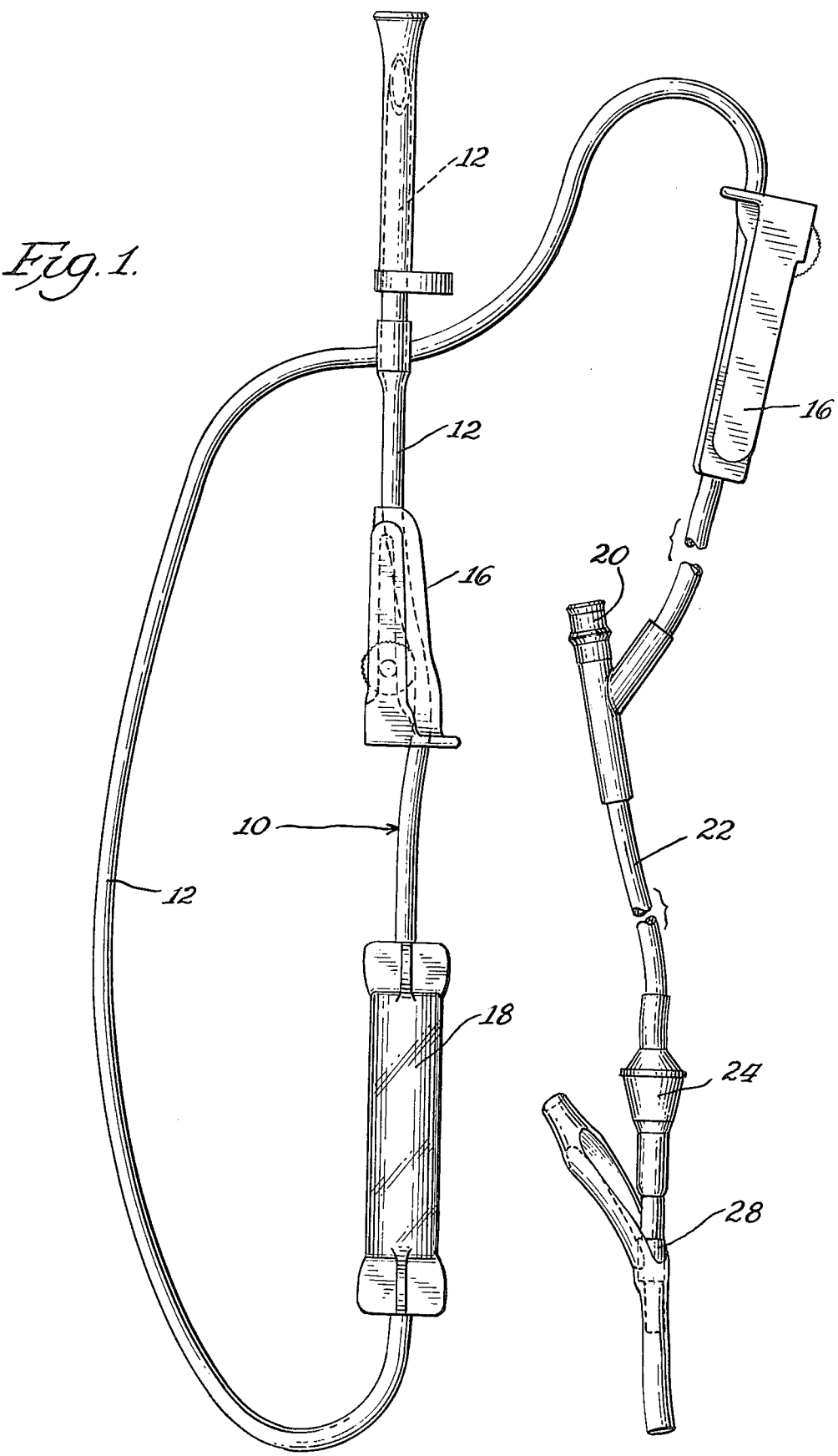

United States Patent [19]

Becker et al.

[11] 4,266,542

[45] May 12, 1981

[54] EVA FORMULATION HAVING IMPROVED PROPERTIES

[75] Inventors: Lawrence F. Becker, Chicago; Leonard F. Czuba, Lombard; Dean G. Laurin, Lake Zurich, all of Ill.

[73] Assignee: Baxter Travenol Laboratories, Inc., Deerfield, Ill.

[21] Appl. No.: 969,637

[22] Filed: Dec. 14, 1978

[51] Int. Cl.$^2$ .................. A61M 5/14; C08L 23/08; C08L 31/04

[52] U.S. Cl. .................. 128/214 R; 525/222; 128/214 C; 128/214.2

[58] Field of Search .................. 525/222; 128/214 R, 128/214 C, 214.2

[56] References Cited

U.S. PATENT DOCUMENTS 3,402,223   9/1968   Hollingsworth .................. 525/229
3,770,852   11/1973   Hager et al. .................. 525/222

*Primary Examiner*—Carman J. Seccuro
*Attorney, Agent, or Firm*—Paul C. Flattery; John P. Kirby, Jr.; Garrettson Ellis

[57] ABSTRACT

A thermoplastic composition is disclosed which consists essentially of a major portion of a first poly(ethylene-vinyl acetate) copolymer which contains from 22 to 30 percent by weight of vinyl acetate units and exhibits a melt index as defined herein of 0.5 to 10. A minor portion of a second poly(ethylene-vinyl acetate) copolymer is included which contains from 25 to 40 percent by weight of vinyl acetate units, the second copolymer exhibiting a melt index of 20 to 1000. The resulting formulation exhibits numerous good properties for use in medical devices, coupled with the capacity for radiation sterilization.

14 Claims, 1 Drawing Figure

U.S. Patent

May 12, 1981

4,266,542

EVA FORMULATION HAVING IMPROVED PROPERTIES

BACKGROUND OF THE INVENTION

Plastic medical devices such as sets for the delivery of intravenous solutions, blood, and the like from a container to a patient are often made of plasticized polyvinyl chloride formulations or the like.

A need, however, exists to make various parenteral solution sets and other devices for use in the medical field out of flexible, transparent plastic materials which may be radiation sterilized, to take advantage of that sterilization technique, while also exhibiting good properties of heat resistance, clarity, low modulus, and dielectric heat sealability, plus solvent sealability for providing a material which can be farbricated with ease.

Furthermore, tubing which is formed from the material most desirably has non-kinking characteristics.

Previously known formulations of poly(ethylene-vinyl acetate) polymers have been known to exhibit the desired resistance to radiation sterilization, making that sterilization technique a possibility for commercial manufacturing of medical devices. However, no formulation has previously exhibited the entire range of the above desired properites, as would be most desirable.

In accordance with this invention, a poly(ethylene-vinyl acetate) (or EVA) formulation is provided in which the above mentioned properties can be achieved simultaneously with a single formulation, along with good stability under radiation sterilization, with the result that parenteral solution and blood sets, as well as other medical devices, may be made from the material of this invention, having optimum characteristics from a material standpoint and also being sterilizable by radiation.

DESCRIPTION OF THE INVENTION

In accordance with this invention, there is disclosed a thermoplastic composition which consists essentially of:

(a) from 75 to 90 percent by weight of a first poly(ethylene-vinyl acetate) copolymer which contains from 22 to 30 percent by weight of vinyl acetate units, said first copolymer exhibiting a melt index of 0.5 to 10; and (b) from 10 to 25 percent by weight of a second poly(ethylene-vinyl acetate) copolymer which contains from 25 to 40 percent by weight of vinyl acetate units, said second copolymer exhibiting a melt index of 20 to approximately 1000.

As described herein, the term "melt index" is defined to mean the melt flow rate as determined by ASTM test D 1238, Condition E.

The resulting preferred formulation exhibits adequate heat resistance for medical purposes to permit autoclaving if desired, coupled with good clarity, relatively low modulus, and sealability by either dielectric or solvent sealing techniques as may be described, for fabrication into blood or solution sets or other medical devices, for example, blood or solution bags or the like. The material also does not kink in the form of small bore tubing as readily as many prior art EVA formulations.

Preferably, if the second copolymer ingredient contains less than 35 percent by weight of vinyl acetate units, its melt index should be at least 30. Generally, the melt index of the second copolymer ingredient is no more than 400, although it can be higher under desired circumstances.

When the second copolymer contains a relatively high amount of 35 to 40 percent by weight of vinyl acetate units, the melt index may go down to about 20, or it may alternatively be high, if desired.

As a general principle with respect to the second copolymer ingredient, when the vinyl acetate content is lower, i.e., in the vicinity of 25 percent by weight, a generally higher melt index material should be used. On the other hand, when the vinyl acetate content is higher, ranging up toward 40 percent, a lower melt index material may be used if desired.

Basically, the first copolymer of this invention is a high-melting, strong, flexible, structural plastic material, but which exhibits certain disadvantages, including a lack of solvent solubility and high molecular weight, which interferes with both solvent and heat sealing. The material also has a tendency to kink when extruded into small bore tubing.

In accordance with this invention, the second copolymer is added to the mixture to impart a more solvent-soluble component to the composition for improving the sealability. Also, the kinking problem is reduced at the same time, along with other advantages. The second copolymer component is chosen to provide sufficient compatability with the first copolymer component so that the material remains transparent, along with the above-described advantages.

Referring to the drawing, a perspective view of a solution administration set utilizing the material of this invention is disclosed.

Administration set 10 includes an upper penetrating spike 12 for penetrating a solution container in a prescribed manner. Flexible tubing 12 and chamber 18, which may be of a conventional size for solution administration sets, may be made by extrusion of the material of this invention. Roller clamps 16 may be provided above and below drip chamber 18.

Supplemental medication site 20 is provided for use in the usual manner, being separated by a second length of tubing 22 made of the material of this invention and similar to the previous tubing 12 from the flashback adaptor 24 which may be made of natural rubber, plus conventional luer adaptor 28 which may be made of a rigid material.

This or any other design of set may be made from the material of this invention, and thus may be sterilized by the exposure to gamma or beta rays in a radiation sterilization system without exhibiting a significant degradation in properties.

Specifically, it is desirable for about 77 to 85 percent of the first copolymer and a corresponding amount of the second copolymer to be present in the composition, particularly when the vinyl acetate content of the first copolymer is 25 to 30 percent by weight and the copolymer has a melt index of 1 to 5 (more specifically 1 to 2).

The second copolymer under these circumstances may preferably have a vinyl acetate content of 30 to 35 percent by weight and a higher melt index, for example, 35 to 50.

The above solution set 10 may be made from a composition which consists essentially of 80 percent by weight of the first EVA copolymer, which first copolymer, in turn, may contain 28 percent by weight of vinyl acetate units and may have a melt index of 1.3. This specific EVA formulation is sold by the U.S. Industrial Chemicals Company under the trade name ULTRATHENE.

This specific composition may also contain 20 percent by weight of a second EVA copolymer which, in turn, may contain 33 percent by weight of vinyl acetate units and a melt index of 43, by the test referenced above. This material is sold by the DuPont Corporation under the trade name ALATHON.

The two ingredients may be conventionally mixed, and then extruded as a homogenous composition into tubing or other desired parts, to fabricate the solution administration set described above or any other desired medical or other type devices. The resulting tubing is clear, flexible, and solvent-bondable, while exhibiting the other advantages of this invention as described above.

The above has been offered for illustrative purposes only, and is not intended to limit the invention of this application, which is as defined by the claims below.

That which is claimed is:

1. A thermoplastic composition which consists essentially of:
   (a) from 75 to 90 percent by weight of a first poly-(ethylene-vinyl acetate) copolymer which contains from 22 to 30 percent by weight of vinyl acetate units, said first copolymer exhibiting a melt index of 0.5 to 10; and
   (b) from 10 to 25 percent by weight of a second poly-(ethylene-vinyl acetate) copolymer which contains from 25 to 40 percent by weight of vinyl acetate units, said second copolymer exhibiting a melt index of 20 to 1000.

2. The composition of claim 1 in which said second copolymer contains from 35 to 40 percent by weight of vinyl acetate units.

3. The composition of claim 1 in which said second copolymer contains less than 35 percent by weight of vinyl acetate units and its melt index is at least 30.

4. The composition of claim 1 in which the melt index of said second copolymer is no more than 400.

5. The composition of claim 1 in which said first copolymer contains 28 percent by weight of vinyl acetate units and has a melt index of 1 to 2.

6. The composition of claim 5 in which said second copolymer has a vinyl acetate content of 33 percent by weight, and a melt index of 35 to 50.

7. The composition of claim 6 in which essentially 80 percent of said first copolymer and 20 percent of said second copolymer are present.

8. A set for administering medical fluid to a patient which comprises a length of flexible tubing, means for communication of said tubing at one end with a source of medical liquid, and means for communication of said tubing at its other end with the patient, said tubing comprising a thermoplastic composition which consists essentially of:
   (a) from 75 to 90 percent by weight of a first poly-(ethylene-vinyl acetate) copolymer which contains from 22 to 30 percent by weight of vinyl acetate units, said first copolymer exhibiting a melt index of 0.5 to 10; and
   (b) from 10 to 25 percent by weight of a second poly-(ethylene-vinyl acetate) copolymer which contains from 25 to 40 percent by weight of vinyl acetate units, said second copolymer exhibiting a melt index of 20 to 1000.

9. The set of claim 8 in which said second copolymer contains from 35 to 40 percent by weight of vinyl acetate units.

10. The set of claim 8 in which said second copolymer contains less than 35 percent by weight of vinyl acetate units and its melt index is at least 30.

11. The set of claim 8 in which the melt index of said second copolymer is no more than 400.

12. The set of claim 8 in which said first copolymer contains 28 percent by weight of vinyl acetate units and has a melt index of 1 to 2.

13. The set of claim 8 in which said second copolymer has a vinyl acetate content of 33 percent by weight, and a melt index of 35 to 50.

14. The set of claim 8 in which essentially 80 percent of said first copolymer and 20 percent of said second copolymer are present.

* * * * *